Oct. 5, 1943. W. H. BATES Plant Pat. 604

PEACH TREE

Filed Oct. 19, 1942

INVENTOR
William H. Bates
BY
Webster & Webster
ATTORNEYS

Patented Oct. 5, 1943

Plant Pat. 604

UNITED STATES PATENT OFFICE

604

PEACH TREE

William H. Bates, Delhi, Calif.

Application October 19, 1942, Serial No. 462,487

1 Claim. (Cl. 47—62)

This discovery relates in general to a new and distinct variety of cling peach; the variety having originated as a chance seedling on my ranch at Delhi, Merced County, California, and was discovered in 1929. The parent tree at the time of its discovery was approximately two years old.

This new variety is a peach particularly desirable for commercial canning, and in appearance, flavor, canning quality, and generally pomological characteristics closely resembles the Lovell peach. However, the Lovell peach is normally a freestone variety, while the herein claimed variety is a clingstone; this being one of the unique and distinguishing features of the variety. Further, as compared to the Lovell peach, the present variety has a smaller stone and a substantially later ripening period.

Since discovery of this new variety, the same has been asexually reproduced, but has not as yet been commercially introduced to the trade.

Figure 1:
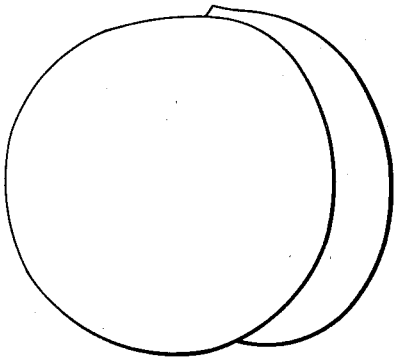
Figure 1 is an outline showing generally the configuration of the fruit.
Figure 2:
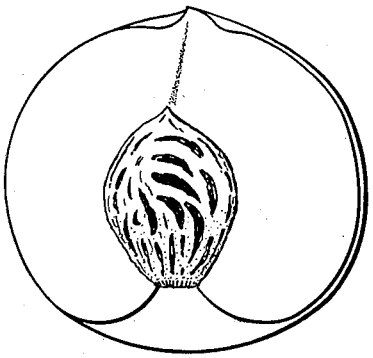
Figure 2 is a sectional view taken axially of the fruit with the stone exposed.

Referring now to the detailed characteristics of my new and distinct variety of peach, the following is a description of the tree and its fruit:

*Tree.*—The tree is of large size, vigorous growth, spreading, open, vase-formed, and a very productive and regular bearer. The trunk of the tree is stocky with medium bark, and the branches are stocky with a medium bark, which is a dull gray-green in color.

*Leaves.*—When well developed, the leaves of the variety are of large size, averageing $6\frac{1}{8}''$ in length and $1\frac{13}{32}''$ in width; being lanceolate, acutely pointed, relatively thin, dark green color, and smooth. The margin is crenate; the petiole is of medium length and thickness; and the glands, which average two in number, are alternate, of medium size, reniform, green in color, and are positioned at the base of the leaf on the petiole.

*Flower buds and flowers.*—The flower buds are obtuse and free, while the flowers are of a medium size, salmon colored, and bloom at a medium date as compared with other varieties; the dates of first and full bloom being on or about March 5th and March 15th, respectively.

*Fruit.*—The fruit is of large size, its average diameter axialy being $2\frac{3}{16}''$, and $2\frac{7}{8}''$ transversely in the suture plane. In shape, the fruit is uniformly unsymmetrical, globose and oblate. The suture is a distinct but shallow line with a slight depression beyond the pistil point. The ventral surface is rounded strongly, and the lips are equal. The cavity is flaring, but elongated in the suture plane with the suture showing on one side. The cavity averages $\frac{11}{32}''$ in depth and $1\frac{1}{16}''$ in breadth. The base is truncate, and the apex short, rounded to truncate and depressed. The pistil point is apical.

The skin of the fruit is bright yellow with a faint marbled blush. Down is moderate, short and does not tend to roll up when rubbed. The skin is of medium thickness and strength and is tenacious to the flesh.

The flesh of the fruit as well as the surface of the pit cavity is yellow. Amygdalin is wanting. The texture of the flesh is firm and fine with few fibers, and ripens quit evenly. The flavor of the flesh is mild and subacid, and the flesh has a distinct aroma.

*Stone.*—The stone of this variety is a clingstone which clearly distinguishes the variety from the Lovell freestone peach. The stone adheres to the flesh over the entire surface along both dorsal and ventral edges. The fibers are long. The stone is of small size, averaging $1\frac{1}{2}''$ in length, $1\frac{3}{16}''$ in breadth and $1\frac{1}{16}''$ in thickness. The form of the stone is oval-elliptical, the base is straight, the hilum oval and the apex rounded. The sides are unequal, curved on the right side. The surface of the stone is regularly furrowed throughout. The ridges are rounded; the pits elongated; and the ventral edge is thick. The stone is of dull-reddish color. The stone has only a slight tendency to split.

*Ripening period of fruit.*—The ripening period of the fruit of the herein described variety of peach is, at Delhi, California, during a period beginning at substantially the end of the ripening period of the Lovell freestone peach; the approximate dates of first and last picking of my new variety being September 8th and September 16th respectively, which is approximately the ripening period of the Phillips cling in the same locality.

*Insects and diseases.*—Resistance to insects and diseases is good.

I have determined by observation, and it is recognized by canners and shippers to whom the fruit has been submitted for experimentation, that the fruit of my new variety of peach has excellent canning and shipping qualities.

In summary, my new and distinct variety of peach, in its general characteristics, greatly resembles the freestone Lovell peach; being unique and distinguishable thereover, however, by its cling stone, its relatively small stone, and the late ripening period of its fruit as compared to said freestone Lovell.

The variety of peach herein described may of course vary in some slight details, due to climatic and soil conditions under which the variety may be grown.

As compared to the Phillips cling, my new variety of peach, as above, has a considerably smaller stone, and very little tendency to split stones and gummosis, which latter are undesirable characteristics of the Phillips cling.

My peach can best be distinguished from the Phillips by the fact that my peach is substantially a Lovell, except for its exceedingly small and cling stone.

Having thus described my discovery, I claim:

A new and distinct variety of peach tree substantially as herein disclosed, having fruit characterized by a substantial general resemblance to the fruit of the Lovell freestone variety of peach but distinguishable therefrom by a cling stone, which is relatively small, and by a later ripening period; said ripening period being substantially that of the Phillips clingstone variety of peach.

WILLIAM H. BATES.